United States Patent [19]
Fertel et al.

[11] Patent Number: 4,937,377
[45] Date of Patent: Jun. 26, 1990

[54] PREPARATION OF 3,4-DIFLUOROBENZOIC ACID BY THE DECARBOXYLATION OF 4,5-DIFLUOROPHTHALIC ANHYDRIDE OR 4,5-DIFLUOROPHTHALIC ACID

[75] Inventors: Lawrence B. Fertel, Buffalo; Neil J. O'Reilly, Grand Island, both of N.Y.

[73] Assignee: Occidental Chemical Corporation, Niagara Falls, N.Y.

[21] Appl. No.: 439,228

[22] Filed: Nov. 20, 1989

[51] Int. Cl.$^5$ ............................................... C07C 5/38
[52] U.S. Cl. .................................................... 562/479
[58] Field of Search ........................................ 562/479

[56] References Cited

FOREIGN PATENT DOCUMENTS 223420   5/1987  European Pat. Off. .
272671   7/1988  European Pat. Off. .
2914915 10/1980  Fed. Rep. of Germany .
123487   7/1985  Japan .

OTHER PUBLICATIONS

Strong, L. et al., J. Solution Chem. 16(2) 105-24 1987.
Rossiter, J. et al., Tehaherdron Lett. 28(43) 5173-4 1987.
C. Wang, Bul. Inst. Kim. Acad. Sinica No. 2156 (1972) (Abstr. CA79 (15):91729) Yakobson, OJ, ZH. Obsch. Khim 36 (1966) pp. 139 (in J. Gen. Chem. USSR, (translated from Russian), 36, (1966) pp. 144.

Primary Examiner—Paul J. Killos
Attorney, Agent, or Firm—James F. Tao; John H. Engelmann

[57] ABSTRACT 4,5-Difluorphthalic anhydride and 4,5-difluorophthalic acid may be decarboxylated in high yield to 3,4-difluorobenzoic acid by heating in N-methyl-2-pyrrolidone or dimethyl acetamide using copper, copper oxide, copper salts, or halides and salts of Zn, Cd, Ag and Ni as a catalyst.

21 Claims, No Drawings

PREPARATION OF 3,4-DIFLUOROBENZOIC ACID BY THE DECARBOXYLATION OF 4,5-DIFLUOROPHTHALIC ANHYDRIDE OR 4,5-DIFLUOROPHTHALIC ACID

BACKGROUND OF THE INVENTION

This invention relates to a method for the preparation of 3,4-difluorobenzoic acid. 3,4-difluorobenzoic acid has been prepared by the oxidation of the corresponding toluene derivative (G. Valkanas, J. Org. Chem., 27 (1962) 2923). More particularly, this invention relates to a process for the preparation of 3,4-difluorobenzoic acid by the decarboxylation of 4,5,-difluorophthalic anhydride or 4,5-difluorophthalic acid in which the decarboxylation reaction is conducted in N-methylpyrrolidone or dimethyl acetamide. Copper catalysts may be used in this reaction.

Many examples of decarboxylation reactions have been reported. Basic substances have been used to catalyze such reactions. For example, it is disclosed in D. S. Tarbell, et al Org. Syn., Coll. Vol. III (1955) 267, that 3,5-dichloro-4-hydroxybenzoic acid may be decarboxylated by vigorous heating in N,N-dimethylaniline. It is disclosed in A. Singer and S. M. McElvane, Org. Syn., Coll. Vol. II (1943) 214, that 3,5-dicarboxy-2,6-dimethylpyridine di-potassium salt may be completely decarboxylated by heating the salt in the presence of calcium hydroxide. Copper and copper salts have been used to catalyze decarboxylation reactions. For example, H. R. Snyder et al, Org. Syn., Coll. Vol. III (1955) 471 disclose the use of a copper oxide catalyst for the decarboxylation of imidazole 4,5-dicarboxylic acid.

Some compounds may be decarboxylated without catalysts. For example, C. Wang, Bul. Inst. Kim. Acad. Sinica, no. 2156 (1972), as abstracted in Chem. Abstracts (CA79 (15): 91729), discloses that tetrachloro or tetrabromophthalic acids, or their anhydrides, may be decarboxylated to the corresponding benzoic acids when refluxed in dimethyl formamide. 3-nitrophthalic acid underwent a similar reaction.

Decarboxylation is not always a predictable reaction. For example, A. S. Sultanov, J. Gen. Chem. (USSR) 16 1835 (1946) as abstracted in CA 41: 6223(e) discloses that salicylic acid may be decarboxylated by autoclaving the acid in the presence of copper bronze and benzene at 170° C. The acid alone decarboxylates at 205° C., while in the presence of aniline decarboxylation begins at 170° C. In the case of salicylic acid, aniline and copper bronze seem to be equal in catalytic ability. On the other hand, when phthalic acid is heated in aniline at 180° C., decarboxylation does not occur and instead phthalic anhydride is produced. Heating phthalic anhydride with copper bronze in chloroform at 180° C. gave a 22% yield of benzoic acid. Phthalic acid was found to decarboxylate to yield benzoic acid merely by heating in water at 235° C.

Decarboxylations of certain fluorophthalic acids have been reported. 3,4,5,6-tetrafluorophthalic acid decarboxylates under certain conditions to yield 2,3,4,5-tetrafluorobenzoic acid. For example, Japanese Patent JP 61/85349 A2[86/85349] as abstracted in Chem. Abstracts (CA105: 153719r), discloses that the reaction may be conducted in an aqueous medium at 150° to 230° C. The reaction may be carried out at a lower temperature (100° to 250° C.) in the presence of copper, zinc, cadmium, iron, cobalt, nickel, other oxides, hydroxides and/or carbonates. Japanese Patent Application 86/103,317 as abstracted in Chem. Abstracts (CA105 (22): 193368u), discloses that the above reaction may be conducted in an aqueous medium at a pH of 0.7–2.2 at a temperature of 100°–200° C. The pH of the medium is adjusted by acidifying with sulfuric acid and partial neutralization with calcium hydroxide. Japanese Patent 63/295529m A2[88/295529] as abstracted in Chem. Abstracts (CA 111 (3): 23221X), discloses that the reaction may be conducted at 130° in tri-butylamine.

Yacobsen, O. J. discloses in Zh. Obsch. Khim. 36 (1966) page 139 (as appearing in Journal of General Chemistry of the U.S.S.R. translated from Russian 36 (1966) page 144), that 2,3,4,5-tetrafluorophthalic acid may be decarboxylated to yield 2,3,4,5-tetrafluorobenzoic acid by heating for one hour at 145° C. in dimethyl formamide solvent.

Japanese Patent JP 01/52737 as abstracted in Chem. Abstract (CA)111 (14): 117305e discloses the preparation of 2,4,5-trifluorobenzoic acid by the decarboxylation of 3,4,6-trifluorophthalic acid in a liquid medium at a temperature of 80°–250° C.

Under slightly more vigorous conditions, Japanese Patent Application 61/43130 A2[86/43130] as abstracted in Chem. Abstracts (CA106 (1): 46295), discloses that 3,4,5,6-tetrafluorophthalic acid may be completely decarboxylated to 1,2,3,4-tetrafluorobenzene. The conditions for complete decarboxylation are in an aqueous medium from 210° to 300° C. with the optional presence of a catalyst.

Japanese Patent Application 86/290399 as abstracted in Chem. Abstracts (CA109 (19) 170038e), discloses that 3,5,6-trifluoro-4-hydroxyphthalic acid may be decarboxylated by heating the compound for three hours, in water, under nitrogen atmosphere, at 140° C. (in a sealed tube) to yield 2,4,5-trifluoro-3-hydroxybenzoic acid.

SUMMARY OF THE INVENTION

We have found that 4,5-difluorophthalic anhydride and 4,5-difluorophthalic acid may be decarboxylated in high yield to 3,4-difluorobenzoic acid in N-methyl-2-pyrrolidone or dimethyl acetamide using copper, copper oxide, copper salts, or halides and salts of Zn, Cd, Ag and Ni as a catalyst.

DETAILED DESCRIPTION OF THE INVENTION 3,4-Difluorobenzoic acid is a useful chemical intermediate. For example, it has been used as an intermediate in the preparation of potential anti-cancer agents. In addition, it has been used in the synthesis of antidepressant drugs. Attempts were made to prepare 3,4-difluorobenzoic acid by decarboxylation of 4,5-difluorophthalic anhydride. 4,5-Difluorophthalic anhydride may be readily prepared by the reaction of 4,5-dichlorophthalic anhydride with potassium fluoride as disclosed in U.S. Pat. No. 4,374,266 (Example I). The acid may be readily prepared by reacting the anhydride with water.

The decarboxylation of 4,5-difluorophthalic anhydride proved to be difficult, since previously known methods of decarboxylation led to a low yield of the desired product along with numerous by-products. The following chart illustrates the decarboxylation methods which were tested. The percentage product shown in the results were those obtained by gas chromatographic analysis, DFBA stands for 3,4-difluorobenzoic acid. s.m. stands for starting material.

DECARBOXYLATION OF 4,5-DIFLUOROPHTHALIC ANHYDRIDE

| Conditions | Results |
|---|---|
| (1) 150–190°/95% $H_2SO_4$ | No Reaction |
| (2) 150 N-methyl-2-pyrrolidone No catalyst | No Reaction |
| (3) 140°/DMF/12 hours No catalyst | 0% DFBA/50% s.m.; 50% other |
| (4) 150° DMAc/$Cu_2O$/22 hours | 19% DFBA/31% s.m./31% other |
| (5) 150° DMAc/CuO/27 hours | 27% DFBA/9% s.m./44% other |
| (6) 150° DMAc/CuO/22 hours | 40% DFBA/12% s.m./36% other |
| (7) 200° Quinoline/Cu/3 hours | 42% DFBA/51% s.m./7% other |
| (8) 190° N-methyl-2-pyrrolidone/ 7 hours | 4% DFBA/74% s.m./22% other |
| (9) 190° DMSO/10% $Cu_2O$/5 hours | many products |
| (10) 190° DMSO/10% CuO/5 hours | many products |

Similarly, the decarboxylation of 4,5-difluorophthalic acid proved to be difficult as well. The decarboxylation was attempted using several methods. The results are shown in the chart below:

REACTIONS WITH 4,5-DIFLUOROPHTHALIC ACID

| Conditions | Results |
|---|---|
| (1) 100° 10% $H_2SO_4$/18 hours | No Reaction |
| (2) 200° 85% $H_2SO_4$ | No Reaction |
| (3) 170° DMSO/18 hours | No Reaction |
| (4) 150° Sulfolane | No Reaction |
| (5) 150° DMSO/LiCl/12 hours | No Reaction |
| (6) 150° DMSO/NaCl/12 hours | No Reaction |
| (7) 125° DMAc/No Catalyst | No Reaction |
| (8) 150° DMAc/22 hours | 0% DFBA, 9% s.m., 91% other |
| (9) 150° DMAc/CuO | 47% DFBA, 2% s.m. 51% other |
| (10) 150° DMAc/$Cu_2O$/22 hours | 69% DFBA, 0% s.m., 31% other |
| (11) 125° DMAc/CuO/22 hours | 60% DFBA, 3% s.m., 37% other |
| (12) 125° DMAc/$Cu_2O$/22 hours | 70% DFBA, 8% s.m., 22% other |

Surprisingly, we have found that 4,5-difluorophthalic anhydride and 4,5-difluorophthalic acid may be selectively decarboxylated in N-methyl-pyrrolidone, dimethyl acetamide or quinoline to yield 3,4-difluorobenzoic acid.

The selective decarboxylation of 4,5-di-fluorophthalic acid or 4,5-difluorophthalic anhydride to yield 3,4-fluorobenzoic acid, may be conducted without a catalyst. However, if no catalyst is used, decarboxylation is conducted in a temperature range of 175°–215° C. In addition, without a catalyst, reactions are rather slow. The decarboxylation is preferably conducted using a copper catalyst such as Cu, $Cu_2O$, CuO, $CuSO_4$, $CuCl_2$, CuCl, $CuF_2$, $Cu_2CO_3$, and $Cu(OH)_2$. In addition, halides and salts of Zn, Cd, Ag and Ni may be used as catalysts. With a catalyst, the reaction may be conducted in a temperature range from about 125°–215° C., with the preferred range being 125°–150° C. The catalyst shows some effect at concentrations as low as 1%. However, it is preferred to use between 5 and 10 percent by weight of catalyst. At any point in the reaction, the degree of starting materials to product can readily be judged by gas chromatographic analysis. However, the reaction is reproducible and once convenient conditions, within the scope of this invention, have been established for conducting the reaction, the gas chromatographic analysis need not be conducted routinely.

The preferred method for conducting this decarboxylation is to use N-methyl-2-pyrrolidone as a solvent, 5 to 10% CuO as a catalyst, and to heat the solution for a period of 2–3 hours. Under these conditions the anhydride and the acid are fully converted to the desired product, and there seem to be no side products detectable by gas chromatography.

The difluorobenzoic acid may be isolated from the reaction mixture by acidifying the mixture and extracting with a suitable solvent such as ethyl acetate or diethyl ether. Evaporation of the solvent yields crude difluorobenzoic acid which may be recrystallized/decolorized by using water and activated carbon.

The following specific examples are provided to further illustrate this invention and the manner in which it may be carried out. It will be understood, however, that the specific details given in the examples have been chosen for purposes of illustration and are not to be construed as a limitation on the invention. In the examples, unless otherwise indicated, all parts and percentages are by weight and all temperatures are in degrees Celsius.

EXAMPLES

EXAMPLE 1

4,5-difluorophthalic anhydride (0.5 grams, 2.7 mmole) was added to a slurry of cupric oxide (5% by weight of starting material) in 5 ml. of N-methyl-2-pyrrolidone. n-tridecane (0.25 grams) was added as an internal standard. The mixture was heated to 190° C. for 3 hours, at which time GC analysis indicated complete consumption of the starting material and conversion to 3,4-difluorobenzoic acid in an 85% yield, based upon the internal standard, corrected for response factors.

EXAMPLE 2

4,5-difluorophthalic acid (0.55 grams, 2.7 mmole) was added to a slurry of cupric oxide (10% by weight of starting material) in 5 ml. of N-methyl-2-pyrrolidone solvent. n-tridecane (0.25 grams) was added as an internal standard. The mixture was heated to 190° C. for 3 hours, at which time GC analysis indicated complete consumption of the starting material and conversion to 3,4-difluorobenzoic acid in an 87% yield, based upon the internal standard, corrected for response factors.

EXAMPLE 3

4,5-difluorophthalic acid (0.55 grams, 2.7 mmole) was added to a slurry of cupric oxide (10% by weight) in dimethyl acetamide. The mixture was heated to 125° C. for 24 hours. Analysis by gas chromatography showed 70% 3,4-difluorobenzoic acid, 8% starting material and 25% other products.

EXAMPLE 4

Using a procedure similar to that of Example 3, 0.55 grams, (2.7 mmole) of 4,5-difluorophthalic acid was added to dimethyl acetamide. 10% $Cu_2O$ as a catalyst was added and the solution was heated at 125° C. for 24 hours. The yield of 3,4-difluorobenzoic acid was 70% (by gas chromatography).

EXAMPLE 5

Using a procedure similar to that of Example 3, 0.55 grams, (2.7 mmole) of 4,5-difluorophthalic acid was added to dimethyl acetamide. $Cu_2O$ as a catalyst was added and the solution was heated at 150° C. for 22 hours. The yield of 3,4-difluorobenzoic acid was 69% (by gas chromatography).

EXAMPLE 6

Using a procedure similar to that of Example 3, 0.5 grams, (2.7 mmole) of decarboxylate 4,5-difluorophthalic anhydride was added to N-methylpyrrolidone. 1% $Cu_2O$ as a catalyst was added and the solution was heated at 190° C. for 30 hours. The yield of 3,4-difluorobenzoic acid was 82% (by gas chromatography).

EXAMPLE 7

Using a procedure similar to that of Example 3, 0.5 grams, (2.7 mmole) of 4,5-difluorophthalic anhydride was added to N-methylpyrrolidone and the solution was heated at 190° C. for 30 hours. The yield of 3,4-difluorobenzoic acid was 79% (by gas chromatography).

We claim:

1. A process for the preparation of 3,4-difluorobenzoic acid which comprises dissolving a starting material selected from the group consisting of 4,5-difluorophthalic anhydride and 4,5-difluorophthalic acid in a solvent selected from the group consisting of dimethyl acetamide, N-methyl-2-pyrrolidone and quinoline to form a solution, and heating said solution at a temperature between 175° and 215° C. until said starting material has been consumed.

2. A process for the preparation of 3,4-difluorobenzoic acid which comprises dissolving 4,5-difluorophthalic anhydride in a solvent selected from the group consisting of dimethyl acetamide, N-methyl-2-pyrrolidone and quinoline to form a solution, adding to the solution a catalytic amount of a catalyst selected from the group consisting of Cu, $Cu_2O$, CuO, copper salts, and oxides and salts of Zn, Cd, Ag and Ni and heating said solution at a temperature between 120° and 215° C. until said 4,5-difluorophthalic anhydride has been consumed.

3. A process for the preparation of 3,4-difluorobenzoic acid which comprises heating dissolving 4,5-difluorophthalic acid in a solvent selected from the group consisting of dimethyl acetamide, N-methyl-2-pyrrolidone and quinoline to form a solution, adding to the solution a catalytic amount of a catalyst selected from the group consisting of Cu, $Cu_2O$, and CuO, copper salts, and oxides and salts of Zn, Cd, Ag and Ni and heating said solution at a temperature between 120° C. to 215° C. until said 4,5-difluorophthalic acid has been consumed.

4. A process according to claim 2 wherein the catalyst is metallic Cu.

5. A process according to claim 2 wherein the catalyst is $Cu_2O$.

6. A process according to claim 2 wherein the catalyst is CuO.

7. A process according to claim 2 wherein the solvent is dimethyl acetamide.

8. A process according to claim 2 wherein the solvent is N-methyl-2-pyrrolidone.

9. A process according to claim 8 wherein the catalyst is 1% $Cu_2O$ and said solution is heated at a temperature of 190° C.

10. A process according to claim 8 wherein the catalyst is 5% CuO and said solution is heated to a temperature of 190° C.

11. A process according to claim 3 wherein the catalyst is metallic Cu.

12. A process according to claim 3 wherein the catalyst is $Cu_2O$.

13. A process according to claim 3 wherein the catalyst is CuO.

14. A process according to claim 3 wherein the solvent is dimethyl acetamide.

15. A process according to claim 14 wherein the catalyst is 10% $Cu_2O$ and said solution is heated at a temperature of 125° C.

16. A process according to claim 3 wherein the solvent is N-methyl-2-pyrrolidone.

17. A process according to claim 16 wherein the catalyst is 10% CuO and said solution is heated at a temperature of 190° C.

18. A process according to claim 2 wherein the solvent is quinoline.

19. A process according to claim 18 wherein the catalyst is Cu and said solution is heated at a temperature of 200° C.

20. A process according to claim 3 wherein the solvent is quinoline.

21. A process according to claim 20 wherein the catalyst is Cu and said solution is heated at a temperature of 200° C.

* * * * *